United States Patent [19]

Arnizen et al.

[11] Patent Number: 5,049,500

[45] Date of Patent: Sep. 17, 1991

[54] POLLEN-MEDIATED GENE TRANSFORMATION IN PLANTS

[75] Inventors: Charles J. Arnizen, Greenville, Del.; Lorin R. DeBonte, Jr., Delran; David A. Evans, Palmyra, both of N.J.; Willie H. Loh, Philadelphia, Pa.; Joan T. O'Dell, Wilmington, Del.

[73] Assignees: E. I. Du Pont de Nemours; DNA Plant Technology, Inc., both of Wilmington, Del.

[21] Appl. No.: 347,831

[22] Filed: May 5, 1989

Related U.S. Application Data

[63] Continuation of Ser. No. 2,845, Jan. 13, 1987, abandoned.

[51] Int. Cl.$^5$ .................. C12N 15/00; A01H 1/00; A01H 1/02
[52] U.S. Cl. .................. 435/172.3; 435/317.1; 435/320.1; 435/172.1; 935/59; 935/64
[58] Field of Search .................. 435/172.3; 47/58

[56] References Cited

FOREIGN PATENT DOCUMENTS

WO85/01856 5/1985 PCT Int'l Appl. .

OTHER PUBLICATIONS

Gupta et al. (1989) Maize Genetic Newsletter, vol. 63, p. 52.
Rhodes et al. (1988) Science, vol. 240, pp. 204–207.
Potrykus (1990) Bio/Technology, Jun., pp. 535–542.
Ohta (1986) Proc. Nat. Acad. Sci., vol. 83, pp. 715–719.
Krens et al. (1984) in IK Vasil, ed., Cell Culture and Somatic Cell Genetics of Plants, vol. 1, Academic Press, N.Y., pp. 522–534.
Maniatis et al. (1982) Molecular Cloning: A Laboratory Manual, Cold Spring Harbor Laboratory, pp. 280–281.
Fromm et al. (1986) Nature 319:791–3.
Ohta, Y. and Sudoh, M., Jap. J. Breed. 30, Suppl. 2:184–185, 1982.
Shillito et al., 1985, Biotechnology 3:1099–1103.
Spielman and Simpson, 1986, Mol. Gen. Genet. 205:34–41.
Lindsey and Jones, 1989, Plant Cell Reports 8:71–74.
Moyne et al., 1989, Plant Cell Reports 8:97–100.

Primary Examiner—Elizabeth C. Weimar
Assistant Examiner—Gary Benzoin
Attorney, Agent, or Firm—Pennie & Edmonds

[57] ABSTRACT

A novel method for efficiently carrying out pollen-mediated gene transformation of flowering plants is described. Utilizing novel DNA constructs incorporating exogenous DNA fragments coding for specific enzymes, the method can product transformed plants exhibiting novel, useful traits. Confirming hybridization tests have been carried out to identify the exogenous DNA transformed into the plant.

2 Claims, 1 Drawing Sheet

POLLEN-MEDIATED GENE TRANSFORMATION IN PLANTS

This application is a continuation of U.S. application Ser. No. 07/002,845, filed Jan. 13, 1987, now abandoned.

TECHNICAL FIELD

This invention relates to a method for efficiently transferring exogenous deoxyribonucleic acid (DNA) fragments incorporating useful traits (genes) and other DNA sequences (promotors, introns, regulatory sequences) into higher plants, and to the resulting transformed plants and seeds.

BACKGROUND OF THE INVENTION

With the advent of genetic engineering, it has become a major goal to modify and improve plants by introducing foreign genes encoding important functional traits. Such traits might include resistance to herbicides, pesticides, or pests; tolerance to cold, heat, drought, or salinity; or improved nutritional quality or yield of specific plant products. The current population explosion and concomitant world food and fiber shortage demand improved productivity in agricultural efforts since virtually all of the readily available, relatively fertile cropland in developed countries has already been placed in use [Science 214: 1087-1089 (1981)]. Modification of monocotyledonous plants including the cereals and many food crops would provide major nutritional and economic benefits.

Two approaches currently exist for transferring heterologous gene(s) or gene sequence(s) into the genome of plants, also known as plant transformation. The first, as described by Chilton et al. [Cell 11: 263-271, (1977)], relies on infection by *Agrobacterium* bacteria, which inserts sequences of a plasmid, known as the Ti-plasmid, into the genome of plant cells. Another approach, described by Lorz et al. [Mol. Genet., 199: 178-182 (1985)], known as direct transformation, induces uptake and integration of plasmid or linearized DNA into the genome of plant protoplasts (which are single cells stripped of cell wall material). The second approach may also use the Ti-plasmid, and has been shown to be efficacious. It is described by Krens et al. [Nature, 296: 72-74 (1982)].

*Aqrobacterium* mediated genetic transfers result from the activity of virulence genes encoded by the Ti-plasmid. The virulence genes effect integration of a region on the Ti-plasmid, designated T-DNA, into the plant genome. When the T-DNA region of the pathogen is manipulated to contain genes of interest, such genes will be integrated into the plant genome following infection. Whole plants, plant tissues, plant cells, and plant protoplasts can all be infected with *Aqrobacterium*.

Alternatively, integration of exogenous genes and gene sequences into plant genomes can be achieved by inducing DNA uptake into plant protoplasts. When protoplasts and DNA molecules are incubated together, under proper inducing conditions (i.e. the use of polyethylene glycol, liposomes and/or electroporation), DNA is taken up and integrated into the plant genome. The frequency of transformation is highly variable, however, and very few major crop plants can be regenerated from protoplasts.

Useful *Aqrobacterium* mediated transformation of dicot tissues and cells is limited, because many of the tissue cultures fail to regenerate plants. For leaf disk transformation, the *Aqrobacterium* Ti-plasmid is modified so that the phytohormone synthesis genes are deleted and so that the T-DNA includes gene(s) of interest. The modified *Aqrobacterium* is incubated with leaf disk explants in tissue culture. Following infection, the bacteria are killed with an antibiotic. Cells of the leaf disks are then induced to regenerate into plants through phytohormone manipulations. Presence of the T-DNA sequence can then be scored if an antibiotic resistance gene had been incorporated as a selective marker. The procedure has proven to be effective for transformation of model systems, i.e. tobacco, petunia, and tomato as described by Horsch et al. [Science, 227: 1229-1231 (1985) ]. However, cells of the leaf disks from many major crop plants, i.e. soybean, corn, wheat, sunflower, etc., will not regenerate into intact plants. The same regeneration problem is encountered in other Aqrobacterium infection systems including other plant tissues, cells, and protoplasts. Therefore, transfer of a gene(s) or gene sequence(s) into cell cultures has no significant impact on major crop plant improvement at this time.

Aqrobacterium mediated plant transformation has been less successful in monocots than dicots. Integration of T-DNA has been demonstrated in only a few non-regenerable monocot systems, namely, Chlorophytum and Narcissus as demonstrated by Hooykaas Van Slogteren et al. [Nature 311: 763-764 (1984)] and Lolium as described by Potrykus et al. [Mol. Gen. Genet. 199: 183-188 (1985)]. At the present time this approach is not considered useful in transformation of major monocot crops, i.e. corn, wheat, rice, etc.

Direct transformation through uptake of plasmid or linearized plasmid DNA by protoplasts is also limited by the requirement to regenerate plants from the protoplasts. None of the major crop plants, i.e. corn, wheat, barley, can be regenerated from protoplasts at frequencies which make the technique acceptable.

Genetic transformation of major crop plants therefore presents a significant problem. The possibility that exogenous DNA might be transferred into germinating pollen grains to modify plant properties has been considered. As the pollen tube emerges from the mature pollen grain, cell wall material is deposited behind the growing tip. Therefore, immediately behind the growing point, the cell wall is just beginning to form. Exogenous DNA may be able to enter the male gametophyte, and be carried to the egg during the course of pollen tube growth and fertilization.

A series of papers by Dieter Hess between 1976 and 1980 reported plant transformation through uptake of intact bacteriophages into germinating pollen [(Hess et al., Z. Pflanzinphysiol., 74: 371-376 (1974)]. In another publication, Hess et al. [Z. Pflanzinphysiol., 77: 247-254 (1976)] describe that *Nicotiana glauca* pollen was incubated with *N. langsdorffii* DNA and that progeny from the treated pollen showed heritable increased tumor formation as normally seen in the sexual cross. Also, Hess [Z. Pflanzinphysiol., 90: 119-132 (1978)] described experiments in which *Petunia hybrida* pollen was treated with lac-transducing phages. Progeny derived from the treated pollen showed improved growth on lactose media. Similar results were obtained by Hess [Z. Pflanzinphysiol., 93: 429-436 (1979)] by treating Petunia pollen with gal transducing phages. He also showed that when pollen from a pure line of *Petunia hybrida* with white flowers was incubated with DNA from red flowered Petunia lines, progeny derived from treated pollen subsequently expressed anthocyanin in the floral parts [Z. Pflanzinphysiol., 98: 321-337 (1980)]. The significance of these studies is not clear, however, since the gene responsible for anthocyanin synthesis has been shown to be hypervariable in embryonic cells and reversion to full expression has been observed at the same frequency as a result of somatic mutations.

PCT Patent Application WO 85/01856 discloses a method for transferring genes between maize inbreds using pollen as a vector comprising the steps of (a) obtaining DNA from a selected donor plant and optionally placing said DNA in a buffer and/or storing it; (b) removing mature pollen from a chosen pollen-donor plant; (c) germinating the pollen; (d) incubating the germinated pollen with the donor DNA; (e) pollinating the pollen-donor plant or other compatible mother plants with the treated pollen; (f) harvesting the resultant seed from the plant; (g) germinating the seed and screening for transformed plants. The method is quite inefficient as demonstrated for maize, however, in that the majority of ears receiving DNA treated pollen produced no caryopses and only 1 to 5 well developed caryopses developed per inflorescence pollinated in those ears which set seed. The maximum number of caryopses produced was 50 per influorescence, compared to between 300 and 500 caryopses following pollination with untreated pollen. In addition, only about 24 percent of the caryopses resulting from the DNA-treated pollen germinated while about 91 percent of untreated caryopses germinated.

Y. Ohta [Proc. Natl. Acad. Sci. U.S.A., 83: 715-719 (1986)] discloses a method for transformation of *Zea mays* Linnaeus. Plants were self-pollinated with pollen which had been incubated with DNA prepared from plant leaves of a corn strain carrying dominant alleles for a set of markers for which the recipient has recessive alleles. The high molecular weight DNA was suspended in 0.3M sucrose at a concentration of 40 ug (u=micro) per mL, and added to fresh pollen from a recipient plant to make a pasty DNA/pollen mixture. The mixture was then placed on the silks of the recipient plant for self-pollination. Maize plants pollinated with the DNA/pollen mixture immediately after it was made produced an average of 135.8 kernels per ear, compared to 146.1 kernels per ear for ears pollinated normally. Phenotypically different kernels were found on four of eight ears to which the mixture was applied. If as little as 5 min. elapsed between the time of preparing the DNA/pollen mixture and placing it on the silks, seed set was drastically reduced and no variant kernels were obtained. About 3.2 percent of the kernels from ears which were pollinated with DNA treated pollen were phenotypically different. Among the variant kernels which germinated, none of the traits segregated as expected in the subsequent generation. Ohta also utilized a procedure whereby the DNA was applied directly to the silk followed by self-pollination. Ears receiving exogenous DNA in this manner showed greatly reduced seed set (3 kernels from 5 ears) and none of them were phenotypically different.

Sanford et al. [Biotechnology and Ecology of Pollen, pp 71.76, eds. D. L. Mulcahy, G. Bergamini, Mulcahy and E. Ottavians, Springer verlag, New York (1986)] attempted to transform wild tobacco, *Nicotiana langsdorffii*, by germinating its pollen in the presence of either *Agrobacterium tumefaciens* or Ti-plasmid DNA. The treated pollen was then used to pollinate the tobacco plants. High rates of abnormal seed development and lethality were noted in the seeds produced by this treatment. Among 800 progeny plants, none synthesized nopaline nor contained T-DNA, as would be expected of Agrobacterium or Ti-plasmid transformation.

Sanford et al. [Theor. Appl. Genet., 69: 571-574 (1985)] subsequently reported unsuccessful attempts to transfer genes via pollen in corn and tomato.

Negrutiu, et al. [Biotechnology and Ecology of Pollen, pp 65-69, eds. D. L. Mulcahy, G. Bergamini, Mulcahy and E. Ottavians, Springer Verlag, New York (1986)] disclose efforts to introduce a plasmid encoding kanamycin resistance into mature germinating tobacco pollen. Tobacco pollen was germinated in the presence of the vector DNA, and various procedures, including heat shock, polyethylene glycol, and electroporation, were employed to induce uptake. Following pollination with the treated pollen, the resulting seeds were collected, germinated and screened for kanamycin resistance. A total of 400,000 seeds were screened but no resistant seedlings were found.

Fromm et al. [Nature, 319: 791-793, (1986)] disclose a plasmid comprising the cauliflower mosaic virus 35S promoter, the gene for neomycin phosphotransferase II (npt-II), and the nopaline synthase 3' region and parts of pBR322 and the use of this plasmid to show that it was transformed by electroporation into maize protoplasts from which arose stably-transformed kanamycin-resistant maize cells. That the exogenous DNA was in the maize cells was demonstrated by hybridizing an appropriate probe to the DNA of the transformed cells.

At this time there exists a clear need for an effective, efficient transformation process which can be used to incorporate exogenous DNA into flowering plants which results in functional expression of the DNA. A process appropriate for monocotyledonous crop plants would provide an opportunity to introduce important additional traits into such crops as corn, wheat, or rice.

SUMMARY OF THE INVENTION

A novel method for efficiently carrying out pollen-mediated gene transformations of flowering plants has been developed. Utilizing novel DNA constructs incorporating exogenous DNA fragments, useful additional traits can be expressed by the plant. Through pollination and subsequent fertilization to give rise to an embryo and ultimately a plant, the transformed pollen produced in the process acts as a vector to transfer exogenous genes into intact plants. Results produced by the instant invention establish that the bacterial coding region for kanamycin resistance has been transferred into corn since the bacterial DNA sequence can be detected in the tissue of plants derived from seeds of plants pollinated in the presence of the exogenous bacterial DNA. Specifically, one aspect of this invention involves a method for transferring exogenous DNA fragments into flowering plants comprising the steps of:

(A) suspending a DNA construct incorporating said exogenous DNA fragment in delivery medium;

(B) contacting the pollen-receptor organs of said plants with the suspension of step A; and (C) contacting said pollen-receptor organs with related ungerminated pollen within a period less than 5 minutes after step (B).

Another aspect of this invention is a DNA construct operable in a flowering plant comprising (a) an exogenous DNA fragment coding for an enzyme functional in said plant, operably linked to (b) a genetic promoter capable of expressing said exogenous DNA fragment such that when said construct is present said plant will synthesize said enzyme thereby enabling said plant to metabolize substances which would otherwise substantially inhibit the growth of said plant. Yet another aspect of the invention is a flowering plant incorporating the DNA construct and the seeds produced by such plants.

DETAILED DESCRIPTION OF THE INVENTION

Figure 1:
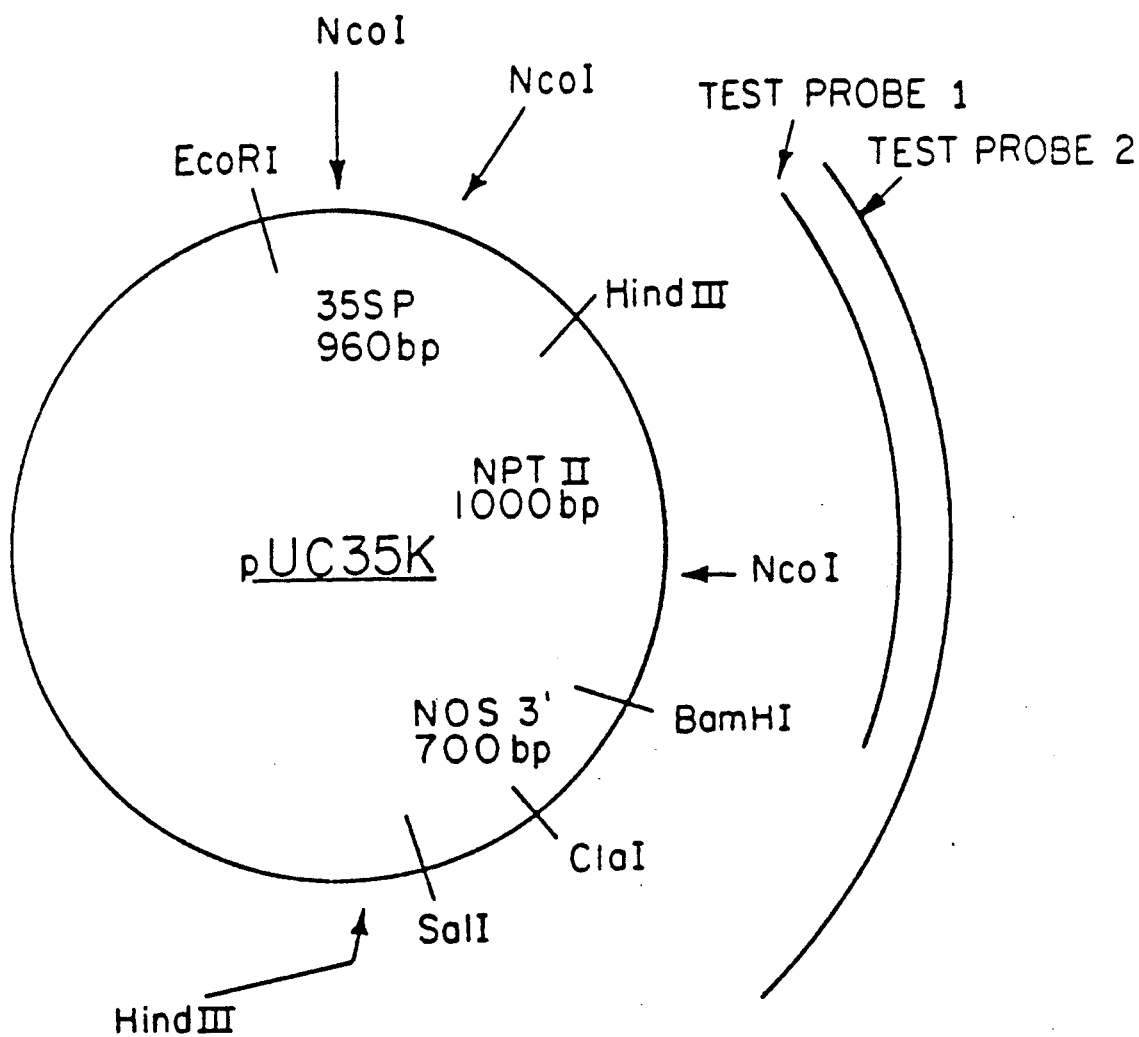
FIG. 1 is the endonuclease restriction map for plasmid pUC35K showing a physical map of the DNA construct encoding a neomycin phosphotransferase II gene conferring kanamycin resistance.

The instant invention provides a method for the pollen-mediated gene transformation of flowering plants which utilizes DNA constructs to transfer additional traits to plants. As used herein, the term "acetolactate synthase" refers to the enzyme which catalyzes the first steps in the biosynthesis of valine, leucine, and isoleucine. Plant acetolactate synthase is sensitive to inhibition by sulfonylurea herbicidal compounds. The term "chimeric gene" refers to a combination of unrelated coding and non-coding sequences of DNA to produce a functional gene. A "DNA construct" includes composites of two or more different DNA sequences that are produced by recombinant DNA techniques for specific purposes, i.e. gene expression, DNA integration, etc. As used herein, the term "DNA sequences" refers to DNA molecules consisting of more than one base pair and includes genes, parts of genes, enhancer regions, promoter regions, regulatory sequences, and non-coding sequences where the specific order for each DNA sequence is of significance in terms of function. The term "enzyme" refers to a protein molecule which catalyzes a chemical reaction. The term "exogenous DNA fragment" refers to any DNA that is not resident in the genome of the plant being transformed. The term "flowering plant" refers to a plant whose seeds are born within a mature ovary. "Herbicide" as used herein, refers to a compound which inhibits the metabolism, growth or replication of plant cells or differentiated plants.

Further, the term "hybridization" refers to the bonding of complementary strands of DNA sequences to form double-stranded DNA. As used herein, the term "gene sequence" refers to DNA sequences which encode a polypeptide chain with functional properties. The term "genetic promotion" refers to DNA sequences to which RNA polymerase binds to initiate gene transcription. As used herein, the term "leaf disk" refers to small, circular patches of tissue from a leaf blade excluding the leaf midrib. The term "pollen" refers to the male gametophyte of a flowering plant prior to germination. The term "ungerminated pollen" refers to pollen grains from which the pollen tube has not formed.

Additionally, as used herein, the term "transformation" refers to genetic modification induced by the introduction of exogenous DNA into a cell. This includes both integration of the exogenous DNA into the host genome, and/or introduction of plasmid DNA containing the exogenous DNA into the plant cell. The term "vector" refers to a plasmid or phage which can act as a vehicle for insertion of exogenous DNA fragments into the genome of a cell.

DNA Construct Containing Kanamycin Resistance

Previous efforts to transfer exogenous gene(s) or gene sequence(s) into the genome of flowering plant cells utilizing pollen have been ambiguous due to the lack of well-defined markers. The genetic transfers discussed in these reports have not been substantiated on the basis of segregation in the progeny. To illustrate the instant process of pollen-mediated transformation, a cloned gene for kanamycin resistance of bacterial origin was utilized. It is envisioned, however, that any vectors and/or DNA sequences can be transferred as effectively as the one chosen to exemplify the invention. Vectors could include but are not limited to plant viral genomes, plasmids derived from bacteria or plants, or phage, or a combination of bacterial and plant DNA sequences. Exogenous DNA could be derived from bacteria, yeast, plants, animals, viruses, or be chemically synthesized, and could, for example, include genes conferring herbicide resistance, increased nutritional value, disease resistance, or tolerance to environmental stresses.

The DNA construct utilized herein consists of the 35S promoter (35S-P) from cauliflower mosaic virus, the neomycin phosphotransferase II (npt II) coding region derived from Tn5, and the termination signal (NOS-3') from a nopaline producing strain of *Agrobacterium tumefaciens*. The plasmid incorporating this DNA construct, pUC35K, was made using techniques well known to those in the art as described by Maniatis et al., Molecular Cloning (A Laboratory Manual), Cold Spring Harbor Laboratory (1982), herein incorporated by reference. The starting plasmid used to construct plasmid pUC35K is plasmid pKNK which in turn is the plasmid pBR322, ATCC accession number 37017 containing a chimeric gene. Plasmid pKNK comprises the ampicillin resistance gene from which the Hind III and Bam HI restriction sites have been removed. The ClaI fragment contains the chimeric gene NOS-P, npt II, NOS-3' for the expression of kanamycin resistance as a selectable marker in plants. The chimeric gene consists of:

(a) a 320 bp ClaI-BqlII sequence containing the promoter region of the neomycin phosphotransferase (NPT II) gene of transposon Tn 5 derived by the conversion of a HindIII site to the ClaI site [Beck, E., Ludwig, G., Auerswald, E. A., Reiss, B. and Schaller, H. Gene 19: 327–336 (1982)].

(b) a 296 bp Sau3A-PstI sequence containing the nopaline synthase promoter (NOS-P) derived from the nopaline synthase gene (NOS) (Nucleotides-263 to +33, with respect to the transcription start site) [Depicker, A., Stachel, S., Dhaese, P., Zambryski, P. and Goodman, H. J. J. Mol. Appl. Genet. 1: 561–574 (1982)] by the creation of a Pst I site at the initiation codon.

(c) the 998 bp HindIII-BamHI sequence containing the coding sequence for the NPT II gene derived from Tn 5 by the creation of HindIII and BamHI sites at nucleotides 1540 and 2518 [Beck, E., Ludwig, G., Auerswald, E. A., Reiss, B. and Schaller, H. Gene 19: 327–336 (1982)], respectively.

(d) the 702 bp BamHI-ClaI sequence containing the 3 foot region of the NOS gene (nucleotides 848 to 1550) [Depicker, A., Stachel, S., Dhaese, P., Zambryski, P. and Goodman, H. J. J. Mol. appl. Genet. 1:561–574 (1982)].

The nucleotide sequence at the fusion of the NOS-P and the NPT coding sequence is:

```
NOS Sequence                    NPTII Sequence
...AATAATCTGCAGCAAGCTTGCGGGGATCSTTCGC ATG...
         PstI        HindIII
```

Plasmid pKNK has been deposited in the American Type Culture Collection with the accession number 67284.

To construct plasmid pUC35K, an EcoRI-HindIII fragment of DNA containing cauliflower mosaic virus DNA sequences between bases 6493 and 7454 of the published sequence was substituted for the pKNK EcoRI-HindIII fragment containing the nopaline synthase promoter (pK35K). This EcoRI-HindIII fragment is known to possess promoter activity. The entire 35S-P-nptII-NOS-3' gene was then removed as an EcoRI-SalI fragment (making use of the SalI site in pBR322) and the fragment was cloned between the EcoRI and SalI sites of pUC13 to generator pUC35K. Plasmid pUC35K is illustrated in FIG. 1. It is deposited in the American Type Culture Collection with the accession number 67285.

General Method for Pollen Transformation

Prior to pollen transformation, immature ear shoots are covered with ear bags to prevent outcrossing. Mature ear shoots are cut back 1 to 1½ inches 18 to 24 hours prior to pollination. At the time of pollination, the covered silks have grown back to form a firm tuft. Plasmid DNA (i.e., pUC35K) which contains the genes or gene sequence(s) desired (i.e., that encodes kanamycin resistance and plant regulatory sequences) was prepared from *Escherichia coli*. To effect pollen transformation, plasmid DNA suspended in a delivery medium is sprayed onto the silks. Mature pollen, previously collected, is immediately placed onto the stigmatic surface and allowed to germinate and grow through the DNA solution. The pollinated ears are immediately covered with brown bags to prevent outcrossing.

In the example of this invention, plants derived from seeds obtained following pollen transformation were subsequently screened for transformation events, i.e., kanamycin resistance. Germinated seedlings were sprayed with kanamycin, which causes localized bleaching of the leaves. Plants which failed to bleach were identified by inspection and rescreened for kanamycin resistance by a leaf disk assay. Leaf disks were placed onto media containing kanamycin. Within a week, bleaching occurs in the leaf disks of kanamycin sensitive plants from the cut surface inward. DNA was extracted from plants which survived both screens and analyzed for the presence of marker DNA by slot blot and Southern analyses.

The following preferred specific embodiments are merely illustrative and not limiting of the remainder of the disclosure. In these examples, all parts and percentages are by weight, and temperatures are set forth in degrees Celsius; unless otherwise stated.

EXAMPLES 1-12

Pollen Transformation

To prepare vector DNA, the *Escherichia coli* strain containing the pUC35K plasmid was batch cultured and the plasmid amplified with chloramphenicol. Plasmid DNA was isolated by a standard procedure described by Maniatis et al. [Molecular Cloning, Cold Spring Harbor Laboratory, Cold Spring Harbor, N.Y., (1982)] and linearized with restriction enzyme EcoRI obtained from Bethesda Research Lab, Gaithersburg, MD 10877). Plasmid DNA containing the DNA construct was added to DNA delivery medium (to achieve a concentration of 10 µg/mL in a solution consisting of 5-10% sucrose, 50 µg/mL boric acid, and 10 µg/mL calcium nitrate). In these experiments, twelve pollen transformation protocols were tested. Polyethylene glycol (PEG) 4000 (J. T. Baker Chemical Co., Phillipsburg, N.J. 08865, Catalog No. U221-8), light paraffin oil (Fisher Scientific, Fair Lawn, N.J. 07410, Catalog No. 0-121) and proteinase K (Sigma Chemical Co., St. Louis, MO 03178, Catalog No. P0390) were added separately to three different preparations of the DNA delivery medium. The concentration of sucrose and PEG was varied so as to maintain the osmotic pressure. The protocols for the twelve experiments are shown in Table I.

In examples 1-9, the DNA solution was applied onto the silks with a Devilbiss No. 15 atomizer. Preliminary experiments have shown that this treatment causes no mechanical damage to the DNA. Each single spray delivers approximately 70 µL of solution. Each ear was sprayed once which delivered 700 ng of pUC35K DNA per ear. In examples 1-6, approximately 0.1 Gm of B-73 pollen was placed onto the silks immediately after the DNA was applied. In examples 7-9, a similar quantity of pollen was mixed with light paraffin oil (1:1, v/v), and applied to the silks as a slurry. After spraying the PGM (Pollen Germination Medium)/DNA solution, each ear received approximately 1 mL of the pollen/oil slurry. In examples 10-12, the procedure outlined by De Wet, Patent Cooperation Treaty, Intl. Publ. No. WO 85/01856, pp 14-15, herein incorporated by reference, was used. Pollen was mixed with a minimal amount of PGM (5 mL of solution on 14 cm diameter petri plates) to form a slurry. After about three minutes, when 10% of the pollen grains had germinated, linearized pUC35K DNA in 1X SSC buffer (8.7 g/L NaCL, 4.4 g/L NaCitrate, pH 7.2) was added to the slurry for a final concentration of 4 µg/mL. After an additional five minutes 15 mL of PGM was added. Two to four mL of the slurry was then applied to each ear by pipette, without exposing the silks to contaminating pollen.

TABLE 1

| Parameters Tested for Pollen Transformation | | | | | |
|---|---|---|---|---|---|
| Example Number | Sucrose | PEG | Added Compound | Method of Application | Method of Pollination |
| 1 | 10% | 0% |  | spray | dry |
| 2 | 5% | 10% |  | spray | dry |
| 3 | 5% | 15% |  | spray | dry |
| 4 | 10% | 0% | proteinase K | spray | dry |
| 5 | 5% | 10% | proteinase K | spray | dry |
| 6 | 5% | 15% | proteinase K | spray | dry |
| 7 | 10% | 0% |  | spray | paraffin oil |
| 8 | 5% | 10% |  | spray | paraffin oil |
| 9 | 5% | 15% |  | spray | paraffin oil |
| 10 | 10% | 0% |  | DeWet | DeWet |
| 11 | 5% | 10% |  | DeWet | Dewet |

TABLE 1-continued

Parameters Tested for Pollen Transformation

| Example Number | Sucrose | PEG | Added Compound | Method of Application | Method of Pollination |
|---|---|---|---|---|---|
| 12 | 5% | 15% | | DeWet | DeWet |

Approximately 1,200 ears of corn, 100 ears for each example were pollinated. Following seed development, each ear was hand harvested and hand shelled. Seeds from twenty ears of each example, selected randomly, were counted and assessed for insect and/or fungal damage. The results are shown in Table 2. The seeds from each ear were kept separate.

TABLE 2

Summary of Corn Seeds Harvested Following Pollen Transformation Experiments

| Example Number | Number of Ears | Average Seed Set (Damaged + Undamaged) | Percent Damage |
|---|---|---|---|
| 1 | 100 | 180.4 ± 81.8 | 4.1 |
| 2 | 102 | 168.1 ± 56.7 | 8.7 |
| 3 | 101 | 219.8 ± 95.3 | 7.7 |
| 4 | 98 | 174.5 ± 74.9 | 11.7 |
| 5 | 95 | 177.0 ± 87.6 | 13.3 |
| 6 | 95 | 90.6 ± 62.2 | 19.7 |
| 7 | 100 | 26.2 ± 42.3 | 40.6 |
| 8 | 98 | 26.5 ± 19.8 | 10.0 |
| 9 | 98 | 16.5 ± 15. | 9.0 |
| 10 | 95 | 0.7 ± 1.6 | 18.2 |
| 11 | 98 | 0.7 ± 2.9 | 20.0 |
| 12 | 88 | 0.2 ± 0.8 | 14.0 |

Seed set ranged from almost half full, normally expected for hand pollination, to extremely low set. Within each example, the set from ear to ear fluctuated widely. Given the overlap in standard deviation values, no correlations can be made between seed set and pollination protocol within an experimental series. High seed set usually leads to good ear development and reduced insect damage. Ears with poor seed set tend to have high numbers of damaged seeds. In examples 10-12, however, the seed set was so low that most of the insect and fungal damage occurred on the naked cob. The first six examples generated close to normal seed set for hand pollination. Seed set was considerably reduced in examples 7-9 in which the pollen was mixed with paraffin oil for application. The procedure reported by De Wet was adopted for examples 10-12 and produced extremely low seed set, less than an average of one seed per ear. Poor seed set results from low pollen viability. When maize pollen is germinated in PGM under the conditions reported by De Wet, most of the pollen lyse within 30 minutes. Our observations suggest that, under these conditions, less than 0.5% of the pollen remains viable when transferred to the ear. Transformation is inherently a low frequency phenomenon, and a procedure which produces low seed set has very limited utility.

In examples 1-6, pollen was added after spraying the DNA on the silks. Using this procedure, seed set is much higher and may approach that obtained through hand pollination. The procedure therefore is a significant improvement over those previously reported. Since the pollen is not submerged in a liquid medium, and germination has not occurred prior to its application to the silks, lysis is minimal. A protocol based on such an approach resulting in higher seed set, can be more realistically exploited to transfer heterologous gene(s) or gene sequence(s) into intact flowering plants.

Screening for Kanamycin-Resistance in Maize

Definitive proof for pollen transformation requires identification of the bacterial neomycin phosphotransferase II DNA sequence in the progeny. However, due to the large number of potential transformants involved, a screening system based on Southern blotting would not be feasible. A protocol to select for kanamycin resistance in tobacco has been developed to assay for Agrobacterium-mediated transformations. We have also developed a mass screening system for corn.

Two assay methods were developed to screen corn plants for resistance to kanamycin. They are (a) foliar application of kanamycin and (b) a leaf disk assay.

(a) Foliar Application of Kanamycin

Intact seedlings of maize, strain B-73 were sprayed six (6) days after germination with a solution containing 500 µg/mL or more of kanamycin (Sigma Chemical Co., St. Louis, Mo. 63178, Catalog No. K-4000) preferably 750 µg/mL and 0.05% Triton X-100 (Eastman Kodak Co., Rochester, N.Y. 14650, Catalog No. 13076). Neither kanamycin, in the above concentrations, nor Triton X-100, by themselves, bring about any bleaching of maize seedlings. The plants are sprayed with the kanamycin-Triton X-100 solution at least 2 consecutive days and as many as 5 consecutive days, preferably 4 consecutive days. The size of the plant container is important in this assay. Bleaching was readily induced when the plants were grown in 196-cavity flats but not so in flats containing larger cavities. Also, plants that were sprayed on cloudy days exhibited much less bleaching even though bleaching was detectable.

(b) Leaf Disk Assay

Leaf disks of B73 corn plants bleach within a week when placed on medium containing 200 µg/mL of kanamycin and 0.5% agarose. Bleaching begins from the cut edge of the disk, and proceeds inward to produce a concentric white outer band. Non-specific yellowing is arrested by adding a cytokinin, e. g. zeatin, 6-benzylaminopurine or kinetin (1 uM) to the solution in which the disks are incubated. Inhibition of yellowing enhances the detection of bleaching.

Combining the above two methods of screening corn plants offers the most reliable basis to select for transformants. Seedlings which are resistant to kanamycin in both assays were tested by slot blot and Southern hybridization for the presence of the bacterial npt II sequence.

Identification of Putative Maize Transformants

Seeds from the pollen transformation experiments, which amounted to approximately 130,000 seeds, were planted into prefilled 196-cavity seedling flats, which were placed onto a porous mat covering the bench-top. Seeds from each cob were planted separately. Developing seedlings received water and nutrients via the porous mat from drip tubes. In addition, the seedlings were hand watered once a day. The seedlings were screened for kanamycin resistance by daily foliar application, beginning six days after germination and at the rate of 100 gallons per acre for four days, of the antibiotic at a concentration of 750 µg/mL.

Plants which exhibited kanamycin damage were discarded. Leaf disks were taken from well developed seedlings which failed to bleach after the spray procedure, and the seedlings were transplanted into 4½ inch pots. Leaf disks respond to kanamycin within five days. Those plants whose leaf disks bleached were discarded. Late germinating seedlings were returned to the bench and resprayed. Leaf disk samples were taken when slower growing seedlings reached approximately six inches in height.

Many of the plants which appeared kanamycin resistant following foliar application were clearly abnormal. The majority of these were stunted. A large frequency of plants also exhibited albino sectoring. Survival of these abnormal plants was extremely low despite careful treatment. Many plants stopped growing and died before transplanting.

Plants which were resistant in both the foliar application and the leaf disk assay were transplanted into 5-gallon pots. Leaf samples were taken from each plant immediately following transplantation.

Analysis of Transformants by Slot Blot and Southern Hybridization

One hundred and sixty-five (165) kanamycin resistant plants have been identified following foliar applications of the antibiotic and the leaf disk assay. DNA from 152 of the 165 kanamycin resistant plants was isolated and analyzed for the presence of the nptII gene sequence. DNA from a normal B73 corn plant served as control DNA so that background levels of reactivity of the probe DNA could be determined. DNA was isolated from 1-2 g of young leaf material as described by Dellaporta et al. [Maize Genet. Coop. News Letter, 57: 26-29 (1983)], with several modifications. Each DNA sample was treated with 50 ug of RNAse A for 25 minutes, then phenol-chloroform extracted twice followed by two chloroform extractions. The 700 uL DNA volumes were precipitated with 500 uL of isopropanol, prior to slot blot and Southern analyses.

Preparation of Probes to Detect the Gene for Kanamycin Resistance

Two hybridization probes were prepared (See FIG. 1). Test probe 1 was prepared by digesting 15 ug of plasmid pKNK DNA with HindIII and BamHI (New England Biolabs, 32 Tozer Road, Beverly, Mass. 01915 9990) in a volume of 100 uL of 100 mM NaCl buffer as directed by the enzyme supplier. Test probe 2 was prepared by digesting plasmid pKNK with HindIII and ClaI (New England Biolabs, 32 Tozer Road, Beverly, Mass. 01915-9990) to obtain a 1.69 kb fragment. While plasmid pKNK was used as the source of the DNA fragments to make the probes for the example in the current experiment, the identical DNA fragments can be isolated from pUC35K by the same procedure. The fragments of DNA resulting from the digestion were separated by electrophoresis in a 1% agarose gel as described by Maniatis et al. [Molecular Cloning, Cold Spring Harbor Laboratory, Cold Spring Harbor, N.Y. (1982)], and in each case, the band of DNA containing the desired fragment (including the 990 bp neomycin phosphotransferase II (nptII) sequence) was purified on NA45 paper (Schleicher and Schuell, 10 Optical Ave., Keene, N. H.) according to the manufacturer's instructions. Approximately 100 ng of the DNA fragments were labeled with 32P-dCTP (deoxycytidine triphosphate) using an oligonucleotide labelling kit from Pharmacia, Inc (800 Centennial Ave., Piscataway, N.J. 08854) and following their instructions.

Slot Blot of DNA

To a 10 ug sample of each DNA preparation, water and 1.6N NaOH were added to bring the final NaOH concentration to 0.4N and the total volume to between 100-400 uL, depending on the initial concentration of each DNA preparation. Each sample of DNA was loaded into a slot of a Schleicher and Schuell Minifold II Slot Blotter (Schleicher and Schuell, 10 Optical Ave., Keene, N. H.) that was set up according to the manufacturer's directions using a Gene Screen Plus (New England Nuclear, Boston, Mass.) blotting membrane. A vacuum was applied to the apparatus to load the DNA onto the membrane. The membrane was removed and air dried. It was then incubated for 5 min on 2 pieces of Whatman 3 MM paper that had been soaked in 0.5N NaOH, 1.5M NaCl, then for 5 min on 3 MM Whatman paper soaked in 0.5 Tris-HCl pH 8.0, 1.5M NaCl, then rinsed in 0.2M Tris-HCL pH 8.0, 2×SSC (Maniatis et al., Molecular Cloning. Cold Spring Harbor Laboratory, Cold Spring Harbor, N.Y. (1982), and air dried. The membrane was incubated at 65° C., for about 5 h in a sealed plastic bag containing 20 mL of prehybridization solution consisting of 1% Sodium Dodecyl Sulfate (SDS), 5×SSC, 2× Denhardt's solution [Denhardt, D. T., Biochem. Biophys. Res. Comm. 23: 641-646 (1966)], and 100 µg/mL heat-denatured carrier DNA as described by Maniatis et al., Molecular Cloning, Cold Spring Harbor Laboratory, Cold Spring Harbor, N.Y. (1982).

Hybridization for Detection of NPT II Sequence

Test probe 1, described above, was heat-denatured and added to 20 mL of hybridization solution of the same composition as the prehybridization solution. The prehybridized membrane was incubated in hybridization solution in a sealed plastic bag at 65° C. for about 20 h. The membrane was removed from the bag, washed twice for 10 min each at 25° C. in 2×SSC, 0.2% SDS, and then washed two more times for 30 min each at 58° C. in 0.1×SSC, 0.2% SDS. The membrane was air dried and exposed to x-ray film. Those samples with hybridization signals greater than those associated with the DNA from the B-73 native corn plants were considered to have DNA homologous to the nptII sequence The results are summarized in Table 3.

TABLE 3

| | Incidence of Kanamycin Resistant and Transformed Plants | | |
|---|---|---|---|
| Example Hybridization Number | Seed Set (Undamaged) Plants | Number of Plants Analyzed | Number with Signal Above Background |
| 1 | 18,040 | 31 | 15 |
| 2 | 17,146 | 13 | 10 |
| 3 | 22,200 | 50 | 27 |
| 4 | 17,101 | 15 | 8 |
| 5 | 16,815 | 10 | 5 |
| 6 | 18,107 | 13 | 8 |
| 7 | 2,620 | 0 | 0 |
| 8 | 2,597 | 15 | 11 |
| 9 | 1,617 | 1 | 0 |
| 10 | 67 | 1 | 0 |
| 11 | 69 | 0 | 0 |
| 12 | 18 | 0 | 0 |

When compared to DNA from control B-73 plants, 84 DNA samples had hybridization signals greater than background. The DNA samples yielded hybridization signals of varying strengths; 17 had strong signals, 31 had intermediate signals and 36 had weaker signals but were nevertheless considered to contain DNA with the nptII gene sequence. Thus, 48 of the 152 plants tested have been transformed with the nptII gene. Pollinations in examples 1-6 and 8 gave the highest incidence of kanamycin resistant plants, many of which were found to contain the bacterial nptII gene sequence by slot blot analysis. No plants derived from the De Wet pollen transformation procedure produced hybridization signals to the NPT II probe stronger than background.

Southern Blot Analysis of Selected Samples

DNA (10 ug) from 10 different kanamycin resistant plants which showed the presence of the nptII gene sequence by the slot blot hybridization test was digested with NcoI (New England Biolabs, 32 Tozer Road, Beverly, Mass. 01915-9990) according to the instructions supplied by the supplier. The resulting fragments were separated by electrophoresis on a 0.7% agarose gel. In a second test, four DNA samples, three from plants different from the above plants were digested with XbaI, (Bethesda Research Laboratories, Life Technologies, Inc., P.O. Box 6009, Gaithersburg, Md. 20877) according to the instructions of the supplier of the enzyme. These were electrophoresed on a 0.7% agarose gel along with samples (10 ug) of undigested DNA from the same four plants. XbaI has no sites in pUC35K. DNA fragments were transferred from the gel to a Gene Screen Plus membrane following the manufacturers instructions (New England Nuclear, Boston, Ma). Prehybridization, hybridization, washing and exposure of the samples to X-ray film were done as described above for testing samples by the slot blot procedure. The probe for the first Southern blot test was test probe 2. The probe for the second Southern blot test was test probe 1. The NcoI digestion produces two fragments from pUC35K that hybridize to the nptII probe: namely, a 1.25 kb fragment that consists of part of the 35S promoter and part of the nptII coding region and a 4.44 kb fragment that contains the rest of the nptII gene and pUC sequences.

Results (a) Fragments from NcoI digest (test probe 2)

Five of the DNA samples from the test plants show hybridization to bands of the sizes described for the pUC35K NcoI digest. Junction fragments with plant genomic DNA have not been detected yet. Three of the DNA samples show hybridization to bands of different sizes indicating rearrangements in the original plasmid, possibly during integration.

(b) Fragments from XbaI digest (test probe 1)

The same major hybridizing band was present in all four DNA samples, both digested and undigested. The hybidizing band is of a size expected for supercoiled plasmid DNA. One plant's DNA contained an additional strongly hybridizing band of slightly larger size, also in both the XbaI digested and undigested samples. Some samples had additional bands of weak hybridization.

The process of selection and screening (foliar spraying and leaf disk assay) in combination with the hybridization analyses (slot blot and Southern blot) demonstrate the presence of npt II sequences (kanamycin resistance) in the corn DNA samples tested.

What is claimed:

1. A method for transferring an exogenous DNA fragment into an incipient embryo of a corn plant comprising the steps of:
   (A) contacting a pollen-receptor organ of a corn plant with a suspension comprising a DNA construct incorporating an exogenous DNA fragment in delivery medium;
   (B) contacting said pollen-receptor organ with compatible ungerminated pollen within a period of less than 5 minutes after step (A).

2. The method of claim 1 wherein the delivery medium further comprises a material selected from the group consisting of polyethylene glycol and protein ase K.

* * * * *